United States Patent [19]

Hershfield

[11] Patent Number: 5,674,687
[45] Date of Patent: Oct. 7, 1997

[54] METHOD FOR IDENTIFYING THE SPECIES ORIGIN OF A DNA SAMPLE

[75] Inventor: Bennett Hershfield, Ithaca, N.Y.

[73] Assignee: Cornell Research Foundation, Inc., Ithaca, N.Y.

[21] Appl. No.: 563,864

[22] Filed: Nov. 29, 1995

Related U.S. Application Data

[63] Continuation of Ser. No. 251,395, May 31, 1994, abandoned.

[51] Int. Cl.$^6$ .............................. C12Q 1/68; C12P 19/34; C07H 21/04; C12N 15/00
[52] U.S. Cl. ........................... 435/6; 435/91.1; 435/91.2; 435/270; 536/23.1; 536/24.33; 536/75.3; 935/76; 935/77; 935/78
[58] Field of Search ............................ 435/6, 91.1, 91.2, 435/183, 270; 536/23.1, 24.33, 25.3; 935/76–78, 1, 8; 436/94

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,717,653 | 1/1988 | Webster, Jr. . |
| 5,075,217 | 12/1991 | Weber . |
| 5,098,824 | 3/1992 | Broad et al. . |
| 5,369,004 | 11/1994 | Polymeropoulos et al. ................ 435/6 |
| 5,378,602 | 1/1995 | Polymeropoulos et al. . |
| 5,387,506 | 2/1995 | Blumenfeld et al. . |

OTHER PUBLICATIONS

Cregan et al., Methods in Molecular and Cellular Biology 5(1):49–61 (1994).
Thomas et al., Theor Appl Genet 86:985–990 (1993).
Mankoo et al., Psychiatric Genetics 2:161–166 (1991).
Hershfield, B. et al., Investigative Ophthalmology & Visual Science 35(4):1612, Abstract No. 1662-33 (1994).
Sung et al., Animal Genetics 24:227–233 (1993).
Roder et al., Mol Gen Genet 246:327–333 (1995).
Estoup et al., Heredity 71:488–496 (1993).
Lieckfeldt et al., Journal of Basic Microbiology 33(6):413–426 (1993).
Glowatzki-Mullis et al., Animal Genetics 26:7–12 (1995).
Schonian et al., Mycoses 36:171–179 (1993).
Vaiman et al., Mammalian Genome 5(5):288–297 (1994).
Smith et al., Genome 37(6):977–983 (1994).
Hershfield et al., Chromosoma 99:125–130 (1990).
Hershfield, et al., Electrophoresis 15:880–884 (1994).
Du et al., Cytogenetics and Cell Genetics 68:107–111 (1995).
Hershfield et al., "Organization and Transcription of Canine $(CAC)_n$ Sequences," *The Journal of Heredity*, May/Jun. 1991, vol. 82, No. 3, pp. 251–254.
S. Ali, et al, "Detection of Genome Specific Monomorphic Loci in *Bos taurus* and *Bubalus bubalis* with Oligodeoxyribonucleotide Probe," *Animal Genetics*, 24:199–202 (1993).
J.T. Epplen, "On Simple Repeated $GA^{tc}A$ Sequences in Animal Genomes: A Critical Reappraisal," *The Journal of Heredity* 79(6):409–417 (1988).
Zietkiewicz, et al., "Genome Fingerprinting by Simple Sequence Repeat (SSR)–Anchored Polymerase Chain Reaction Amplification," *Genomics*, 20:176–183 (1994).

*Primary Examiner*—Bradley L. Sisson
*Attorney, Agent, or Firm*—Nixon, Hargrave, Devans & Doyle

[57] ABSTRACT

Microsatellite nucleotide repeat sequences present in DNA isolated from a biological sample are used to determine the origin of a biological sample by a process including the steps of isolating nucleic acid from a biological sample, determining the interspersion pattern of repeats of a nucleotide sequence selected from the group consisting of di-, tri-, and tetra- microsatellite nucleotide repeat sequences in the DNA, and comparing the determined interspersion pattern with known interspersion patterns of the nucleotide sequence in selected mammalian species.

Species-specific, individually-invariant interspersion patterns of di-, tri-, or tetra- microsatellite nucleotide repeats in vertebrate DNA samples are identified by a process including the step of annealing separated strands with a oligonucleotide primer selected from the group consisting of di-, tri- and tetra- microsatellite nucleotide repeat sequences at a concentration ratio of primer to DNA template of less than about 2500:1, the annealing being conducted at a temperature greater than about 30° C. and in the presence of magnesium ions at a concentration less than about 3.0 mM, to produce an extension product of the primer which is complementary to the strand of the DNA sample.

9 Claims, 2 Drawing Sheets

METHOD FOR IDENTIFYING THE SPECIES ORIGIN OF A DNA SAMPLE

This application is a continuation of application Ser. No. 08/251,395, filed May 31, 1994 abandoned.

FIELD OF THE INVENTION

The present invention relates to use of nucleotide repeat sequences present in DNA isolated from a biological staple to determine the origin of the biological sample.

BACKGROUND OF THE INVENTION

Biological samples are collected and analyzed for a variety of reasons relating to, for example, criminal forensics or agricultural forensics (e.g., to identify individuals for paternity, immigration, criminal suspect lists, or population genetics studies). The known methods of analyzing such biological samples involve using the nucleic acids to identify individually specific patterns within a species. For example, the procedures collectively referred to as "DNA fingerprinting" utilize minisatellite (e.g., a tandemly repeated DNA sequence having a total size from about a few hundred to a few thousand bases) and microsatellite (e.g., tandemly repeated DNA sequence having a total size of up to about 100 bases) probes to obtain highly specific patterns which are useful to, for example, identify individuals within a known species or in pedigree studies to determine lineage. See, e.g., Jeffreys et al., *The Efficiency of Multilocus DNA Fingerprint Probes for Individualization and Establishment of Family Relationships, Determined From Extensive Casework*, 48 Am. J. Hum. Genet. 824–840 (1991). Methods such as DNA fingerprinting are not useful in identifying one species from another because they utilize patterns that are individually-specific and complex (i.e., many different bands in the amplification pattern) and, as a result, are not capable of differentiating between unknown species that may have contributed to the sample.

The known processes for identifying one species from another generally rely on protein electrophoresis techniques, enzyme linked immunosorbent assay ("ELISA") or radioimmunoassay ("RIA") processes. However, because those procedures depend on antibody recognition or isozyme resolution, they are useful only when the material contains a contribution from a suspected species. That is, the test must be separately performed relative to each suspected species to exclude that species as a possible contributor.

U.S. Pat. No. 5,075,217 to Weber ("Weber") discloses a product and process for characterizing the human genome utilizing polymorphic DNA fragments containing certain nucleotide sequences. Weber is useful to identify individual humans by evaluating the polymorphic fragments containing certain tandem repeat sequences. Weber, however, does not provide any suggestion of a method for identifying one species from another.

U.S. Pat. No. 5,098,824 to Broad et al. ("Broad") discloses certain polynucleotide sequences capable of selectively hybridizing to Equidae DNA and a method of distinguishing Equidae DNA (e.g., horse, donkey, and zebra DNA) from that of other animals. Unfortunately, Broad's teachings have no applicability in species identification other than for Equidae DNA.

Likewise, the methods described in S. Ali et al., "*Detection of genome specific monomorphic loci in Bos taurus and Bubalus bubalis with oligodeoxyribonucleotide probe,*" 24 Animal Genetics 199–202 (1993)("Ali") are not useful for identifying the species that has contributed to a biological sample. Like Broad, Ali's experimentation focused on individual animals from animal species with very similar gene pools (e.g., cow and buffalo) using hybridization techniques. Ali merely discloses that the overall hybridization pattern relative to certain enzyme and probe combinations are unique to one or the other species. However, different individuals from the same species have different patterns in Ali's technique. (See, e.g., Ali FIG. 3, Lanes 3 and 4 (bonnett monkey) and Lanes 15 and 16 (catfish)).

Polymerase chain reaction ("PCR") techniques have been increasingly used in recent years to undertake genetic analysis. PCR is a method of selectively and repeatedly replicating selected segments from a complex DNA mixture. This ability to amplify discrete nucleotide sequences has led to greatly increased sensitivity in genetic testing and has been shown to be useful in differentiating between individuals of a given species.

The general PCR process involves first isolating DNA from a biological sample (e.g., blood, hair, semen). The DNA, in the presence of a buffer containing $Mg^{+2}$ ions (usually added in the form of $MgCl_2$), deoxynucleotides, oligonucleotide primers and a replicative enzyme (e.g., Taq polymerase), is heat-denatured (e.g., at 90° to 95° C.). The heat-denaturation causes the DNA strand to become single stranded. Cooling the denatured strands (e.g., at temperatures ranging from room temperature to 65° C.) constitutes "annealing", during which the primers hybridize to complementary sequences on the template DNA. The replicative enzyme incorporates complementary bases in, typically, a 3' to 5' direction from the locus of the primer:template duplex. The enzyme will extend (e.g., promote complementary incorporation of base pairs on the chain) the primers at high temperatures (e.g., up to 72° C.).

Once synthesis (e.g., extension) is complete, the whole solution is heated further (e.g., up to 95° C.) to denature the newly formed DNA duplexes. When the temperature is lowered, another round of synthesis will occur due to the vast molar excess of primer still present in the solution. The cycle of denaturation and synthesis can be continually repeated as desired, doubling the amount of the sequences of interest after each cycle. Thus, the sequence of interest can be replicated exponentially using PCR methodologies. In this way, specific DNA regions can be examined quickly, starting from small samples of DNA.

As stated above, PCR processes have been used extensively to produce and compare amplification patterns between individuals of the same species. See, e.g., J. Welsh and M. McClelland, 18 *Nucl. Acids Res.* 7213–18 (1990) (relating to arbitrarily primed PCR processes); J. G. Williams et al., 18 Nucl. Acids Res. 6531–35 (1990)(describing a process for producing randomly amplified polymorphic DNA); and G. Caetano-Anolles et al., 9 Biotechnology 553–57 (1991)(describing DNA amplification fingerprinting processes). In each of the above-cited processes, random sequences within the given genome were amplified. The above-cited PCR processes teach that when amplifying random sequences, it is frequently necessary to relax PCR conditions to produce useful PCR amplification products that can be differentiated between individuals of a known species. For example, processes like those cited above will conduct initial rounds of annealing (1) at reduced temperatures (e.g., as low as 30° C.), (2) use very high magnesium concentrations (e.g., as high 8 mM), and/or (3) use very high ratios of primer to DNA template (e.g., 100,000 to 1).

The PCR amplification processes conducted under those conditions have been found to produce amplification products with a marked variability between individuals of the same species and are very complex and difficult to interpret. Accordingly, the known PCR processes do not provide a useful methodology for producing species-specific, individually-invariant PCR amplification products.

Ideally, a method for species identification of bloodstains or other biological samples would produce easily interpretable quick results in a single experiment that could definitively discriminate which species contributed to a given biological sample, independent of any prior assumptions of contribution by the investigator. As discussed above, the known processes for discriminating between species contributing to a biological sample cannot accomplish those goals and, accordingly, new methods of species identification of contributors to biological samples are needed.

SUMMARY OF THE INVENTION

The present invention relates to use of nucleotide repeat sequences present in nucleic acid isolated from a biological sample to determine the origin of the biological sample. More specifically, the present invention relates to a method of identifying the origin of nucleic acid samples from DNA-containing organisms and includes the steps of isolating nucleic acid from a biological sample and determining the interspersion pattern of repeats of a sequence selected from the group consisting of di-, tri-, and tetra- microsatellite nucleotide repeat sequences in the isolated nucleic acid. Next, the determined interspersion pattern can then be compared with known interspersion patterns of the microsatellite nucleotide sequence in selected DNA-containing organisms to determine the species contributing to the biological sample.

In another embodiment, a PCR method that facilitates the recognition of microsatellite sequences that are species-specific and individually invariant is disclosed. That method includes the steps of first providing a sample of DNA having two complementary strands and denaturing the DNA sample for a time and temperature effective to cleave the strands of the sample. Next, the separated strands are annealed with an oligonucleotide primer. The oligonucleotide primer is selected from the group consisting of primers complementary to a nucleotide repeat sequence selected from the group consisting of di-, tri- and tetra- microsatellite nucleotide repeat sequences. The annealing reaction is conducted at a temperature greater than about 30° C., preferably at or above about 45° C. and in the presence of magnesium ions at a concentration less than about 3.0 mM. After annealing, extension is accomplished by binding the added nucleotides to the complementary nucleotides on the primer-annealed strands of DNA to produce double stranded extension products having a specific di-, tri- or tetra- microsatellite nucleotide repeat sequence at one or both of the products' 3' and/or 5' ends. The denaturing, annealing, and extension steps are repeated a sufficient number of cycles to produce amplification products capable of being analyzed to determine an interspersion pattern of the subject nucleotide repeat sequence in the DNA sample.

The process of the present invention provides a quick, definitive test for determining the contributor(s) to a biological sample and requires no prior assumptions or independent investigation on the part of the investigator to be used effectively.

DETAILED DESCRIPTION OF THE INVENTION

Figure 1:
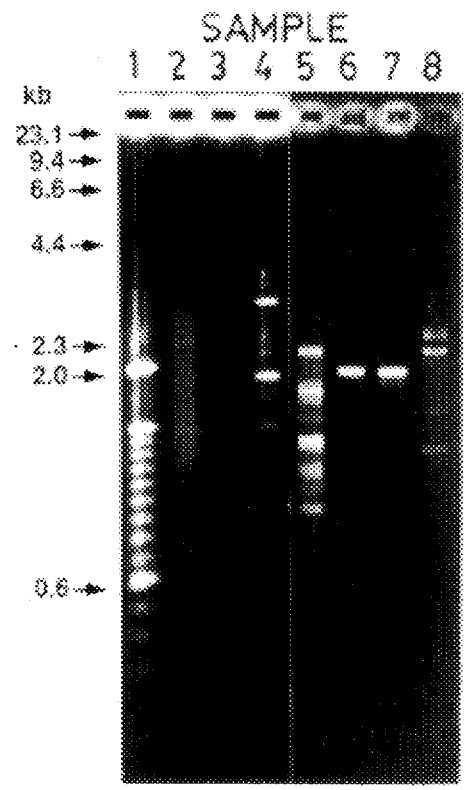
FIG. 1 is a photograph of the results of the $(CAC)_n$ amplification and electrophoretic analysis performed on DNA from individuals of several non-human vertebrate species.

The present invention relates to a method of identifying the origin of nucleic acid samples from DNA-containing organisms. The present process includes the steps of isolating nucleic acid from a biological sample and determining the interspersion pattern of repeats of a sequence selected from the group consisting of di-, tri-, and tetra- microsatellite nucleotide repeat sequences in the isolated DNA. For the purposes of the present invention, an "interspersion pattern" is defined as the pattern of repeats of a specific microsatellite nucleotide sequence as determined by evaluating the number of nucleotides separating each of the repeat sequences in a sample of DNA. The interspersion pattern determined in accordance with the present invention has three aspects: (1) the number of bands which include the specific microsatellite nucleotide sequence being evaluated at one or both of their 3' and/or 5' ends, (2) the relative size (i.e., the number of base pairs comprising a band) of the bands, and (3) the relative intensity of each band (i.e., the degree of amplification of a given band). For purposes of the present invention, a "band" is a sequence of nucleotides contained in the DNA of a DNA-containing organism which has as one or both its 3' and/or 5' ends a repeat sequence selected from the group consisting of di-, tri-, and tetra- microsatellite nucleotide repeat sequences. In the present application, nucleotide repeat sequences will be represented as the nucleotide sequence in parentheses with the subscript "n" appearing outside the parentheses (e.g., "$(CAC)_n$"). n is defined as a variable representing the number of repeats of the sequence of interest present at any one locus of the genome of the DNA sample being evaluated. It is understood that the number of repeat sequences appearing at any one locus in DNA varies widely. That fact does not affect the utility of the present invention because the present method evaluates the interspersion pattern of the repeat sequence of interest in a DNA sample and does not depend on determining the specific number of repeats in any one sequence at any one or more loci in the sample.

The determined interspersion pattern can be compared with known interspersion patterns of the specific microsatellite nucleotide sequence in other DNA-containing organisms to identify the species contributing to the biological sample.

The present method can be used to differentiate the DNA of DNA-containing species. Any biological sample containing DNA can be used in the method of the present invention. Of course, the present invention will likely have its greatest utility in differentiating and identifying vertebrate species which may or may not have contributed to a given biological sample. Common biological samples from which DNA is extracted include blood, lymph tissue, semen, hair, feathers and skin.

DNA can be isolated from the biological sample by any known process or protocols such as those disclosed in E. R. B. McCabe, 1 *PCR Methods and Applications* 99–106 (November 1991). An exemplary process for removing and isolating DNA from a biological sample is described in Hershfield et al., *Cloning of a Polymorphic Canine Genetic Marker Which Maps to Human Chromosome 9,24* Anim. Genet. 293–295 (1993).

The method of the present invention is especially advantageous because it requires only very minute amounts of DNA to produce reliable results. Amounts of DNA less than 100 picograms can be utilized in the method of the present invention.

Once the DNA has been extracted and isolated from the biological sample, the interspersion pattern of repeats of a preselected di, tri-, or tetra-microsatellite nucleotide sequence (or its complement) is determined. The interspersion pattern of the selected repeat sequence can be determined by any known process of evaluating. A preferred method of determining the interspersion pattern of the predetermined repeat sequence is by polymerase chain reaction ("PCR") techniques. Generally, PCR involves the steps of providing a sample of DNA to serve as a template for the PCR reaction, denaturing the DNA to form two complementary strands of the DNA sample, and annealing the denatured DNA with a "primer" which is complementary to the 3' and/or the 5' end of sequence to be amplified. Conventional PCR processes which amplify individual-specific random sequences relax the PCR conditions (e.g., conduct initial rounds of primer annealing at reduced temperatures, maintain very high concentrations of magnesium, utilize very high ratios (100,000:1) of primer to DNA template). It has been unexpectedly discovered in accordance with the present invention that modifying those conditions and using specific types of primers will facilitate identification of species-specific and individually-invariant nucleotide repeat sequences.

The use of PCR according to the present invention requires first denaturing the extracted and/or isolated DNA sample (also referred to herein as "DNA template") for a time and temperature effective to cleave the complementary strands of the DNA sample and form separated strands of the DNA sample. Typically, the conditions required to denature (i.e., separate) the double stranded DNA will also effectively break the DNA into smaller fragments (i.e., pieces of the DNA template having fewer base pairs).

Denaturation can be accomplished by any suitable denaturing method including physical, chemical, or enzymatic means. One physical method of separating the strands of the nucleic acid involves heating the nucleic acid until it is completely (>99%) denatured. Typically, heat denaturation is conducted at temperatures ranging from about 80° to 105° C. for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for denaturing nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., DNA Helicases 63–67; and techniques for using RecA are reviewed in C. Radding, 16 *Ann. Rev. Genetics* 405–37 (1982). Although, as disclosed above, denaturing conditions will generally serve to break the DNA strand into smaller fragments (which are more suitable for PCR analysis in accordance with the present invention), restriction enzymes can also be used to further limit the size of the DNA fragments to be used as the initial DNA template for the PCR process.

Preferably, denaturation is accomplished by heating at a temperature of about 92° to 96° C., most preferably about 94° C., for about one minute.

After the DNA sample has been denatured and fragmented sufficiently, the separated and fragmented strands are reacted with an oligonucleotide primer selected from the group consisting of di-, tri- and tetra- microsatellite nucleotide repeat sequences to anneal the oligonucleotide primer to complementary base pairs on the denatured and fragmented strands of the DNA sample. The annealing reaction serves to initiate production of strands complementary to the strands of the DNA sample which contain the microsatellite nucleotide repeat sequence of interest. After annealing, production of complementary strands is completed by an extension reaction which includes the addition of deoxynucleotides to complementary base pairs on the denatured and fragmented strands of DNA. Primer extension generally begins from the 3' end of each annealed primer and proceeds in the 5' direction along the DNA template. Therefore, in sum, the production of strands complementary to strands of the DNA template which contain the repeat sequence of interest includes the steps of primer annealing (i.e., the hybridization of the primer to its complementary sequence in the DNA sample) and primer extension (i.e., the incorporation of deoxynucleotides into a complementary sequence of nucleotides on the DNA strand being amplified).

As disclosed supra, the primer is selected from the group consisting of di-, tri- and tetra- microsatellite nucleotide repeat sequences. Preferably, the primer is selected from the group consisting of the nucleotide sequences CAC, GTG, GATA, TCC, AGG, CTAT, CA or TG. Most preferably the microsatellite nucleotide sequence is CAC or GTG.

The concentration of primer in the PCR reaction mixture is dependent upon the amount of DNA template used, reaction conditions and reagents used (e.g., pH, temperature, magnesium concentration, use of specificity-enhancing compounds). Although the present PCR process can utilize primer:template ratios up to 100,000:1, for maximum reproducibility and reliability of the process, it is preferred to use primer:template ratios less than 2500:1.

The time and temperature conditions for the "primer annealing" portion of the PCR reaction are dependent upon the base composition, length and concentration of the amplification primer used. In general, the smaller the primer, the lower the annealing temperature. However, in the method of the present invention, all primer annealing (including initial cycles) is conducted at a temperature greater than about 30° C., most preferably greater than or equal to about 45° C.

Magnesium concentration in the present PCR process can vary, depending on reaction conditions and reagents used. As disclosed above, the method of the present invention does not require high concentrations of magnesium to be effective and can achieve excellent results using low magnesium concentrations. The preferred magnesium concentration in the present process is in the range of about 1.5 to 3.5 mM. The present PCR process is preferably carried out at a pH less than (i.e., more acidic) about 9.5.

Primer extension will occur after the primer has annealed to its complementary sequence in the DNA sample and when in the presence of deoxynucleotides and an agent for polymerization that will act as a catalyst for primer extension. The agent for polymerization can be any compound or system which will function to accomplish the synthesis of primer extension products, including enzymes. Suitable enzymes for this purpose include, for example, Taq polymerase, vent polymerase, E. coli DNA polymerase I, Klenow fragment of E. coli DNA polymerase I, T4 DNA polymerase, and other available DNA polymerases, reverse transcriptase, and other enzymes, including heat stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There are agents, however, which initiate synthesis at the 5' end and proceed in the other direction, using the same process as described above. The preferred polymerization agent is Taq polymerase (available from Perkin-Elmer Cetus).

The concentration of the polymerization agent in the PCR reaction mixture varies depending on the individual DNA template and primer used. Typically, for example, the concentration of Taq polymerase should be between about 0.25 to 6 units per 100 μl of reaction mixture. Preferably, the concentration of Taq polymerase is between about 0.5 to 2.5 units per 100 μl of reaction mixture.

Primer extension should be conducted at temperatures in the range of 50° to 90° C., preferably 65° to 75° C. and, most preferably, at a temperature of about 72° C. Primer annealing can continue for a time in the range of up to about 10 minutes and normally should continue for at least about one minute. However, extension can often occur sufficiently upon (and substantially concurrent with) primer annealing without any change in conditions or time delay. On the other hand, longer extension times can be used in early cycles if the DNA template concentration is very low, and at late cycles when the primer extension product concentration can exceed enzyme concentration.

The cycle of denaturing, annealing and extending can be repeated as often as necessary to produce a PCR amplification product that can be analyzed to determine the interspersion pattern of the repeat sequence of interest. Generally, the cycle should be repeated at least about 20 times, most preferably about 40 times. In cases where low initial template counts exist, up to 80 cycles or more can be necessary to produce a product which can be evaluated.

For example, if the repeat sequence of interest was $(GTG)_n$, the primer added to the PCR solution would be, for example, 3'-$(CAC.)_n$-5'. The primer, added in great molar excess relative to the DNA template, would search out and bind to complementary $(GTG)_n$ sequences interspersed throughout the fragments of single stranded DNA template contained in the PCR solution. In the locations where the primer has bound to its complement, extension will then proceed from the 3' and/or 5' end of the fragments in the presence of deoxynucleotides and appropriate polymerization catalysts, thereby providing double stranded DNA fragments within the DNA template which have $(GTG)_n$ as one or both of their 3' and/or 5' end. The repeated cycles of denaturing, annealing and extending will result in amplification bands in the DNA template having $(GTG)_n$. at one or both of their 3' and/or 5' ends.

Further detail regarding the use of PCR are disclosed in U.S. Pat. Nos. 4,683,195 to Mullis et al. and 4,683,202 to Mullis et al. and in Innis et al., *PCR Protocols—A Guide To Methods And Applications*, (1990), the disclosures of which are hereby incorporated by reference.

The amplification products produced by PCR (or any other suitable method as discussed supra) can be quantified by any suitable method including high pressure liquid chromatography ("HPLC"), electron microscopy, and gel electrophoresis. Quantification of the amplification product allows comparison of the amplification product of a specific unknown sample with the amplification product of known samples. In that manner, the identity of a species contributing to a biological sample can be determined. The preferred method of analyzing the PCR amplification results is by gel electrophoresis, an example of which is described below.

Gel electrophoresis involves the general steps of providing a conducting material through which an electrical current can pass. The conducting material must also be somewhat porous, thus allowing diffusion of liquid through the material. Typically the conducting material is a block or slab of solid or semi-solid material such as agarose acrylamide or starch. Preferably, an agarose gel in a concentration of 1 to 1.5 grams agarose per 100 ml gel is used as a conducting material.

A series of longitudinal indentations are made in the conducting material. The amplification product of the PCR process is then placed in a buffered loading solution to form a liquid containing the amplification product. The amplification product sample is placed in each of the indentations in the conducting material and a current is applied to the gel and, by extension, the amplification product sample. Because DNA is negatively charged, it will migrate to the positive pole of the charged conducting material. However, the rate of migration of the amplification product (which contains a variety of different-sized bands) will be dependent on the rate of diffusion of a given band through the conducting material. Smaller bands will diffuse more quickly through the conducting material toward the positive pole than will larger bands. To quantify the differences in the rate of diffusion of various bands as a product of the bands' size, a "marker" is often used which serves as a reference to evaluate the size of the bands diffusing through the conducting material. The marker contains bands of nucleic acid material of known size which will migrate at a certain rate based on the bands' respective sizes. Therefore, after the current is removed, the location of the known bands of the marker can be used to create a logarithmic scale on the conducting material. That is, the evaluator can observe the marker bands on the conducting material and determine how far toward the positive pole a band containing, for example, 2.7 kilobase pairs would migrate.

The current is removed after the desired time, which ranges generally from 30 minutes to overnight. The time can be adjusted according to a variety of factors such as, for example, the porosity of the conducting material, the strength of the current, or the size of the bands.

After the current is removed, the DNA is stained with a material capable of being illuminated (e.g., exhibiting fluorescence, phosphorescence) upon exposure to activating radiation. For example, DNA can be stained with ethidium bromide which will phosphoresce upon exposure to shortwave ultraviolet radiation. Alternatively, use of radioactive deoxynucleotides (or other labelled compounds such as biotin, digoxygenin, or horseradish peroxidase) during PCR permits detection on X-ray film or by chromogenic detection processes. The illuminated bands of DNA can then be photographed and compared to the markers to determine the size of the bands in the amplification product. In addition, the bands which were amplified in greater numbers will absorb a relatively greater quantity of the illuminating material and will, in turn, exhibit a greater intensity of illumination. The relative intensity of the various bands amplified in the PCR process can then be visually compared or more precisely measured using, for example, a densitometer or fluorimeter.

Therefore, once the amplification process and electrophoresis has been completed for a given DNA sample of known origin, empiric indicia (e.g., number of bands containing the specific repeat sequence of interest, relative size of the bands, degree of amplification of each band) of the interspersion pattern of that specific repeat sequence in the DNA sample has been created. The resulting indicia of the interspersion pattern of interest can then be compared to the similarly quantified interspersion patterns of known DNA-containing organisms to identify the species contributing to the DNA sample being examined.

The present method can be extremely useful in animal forensics to determine the species of the contributor(s) to a DNA-containing biological sample. The present method can also be used as a method of marking recombinant organisms. That method would include the steps of introducing an atypical interspersion pattern of repeats of a nucleotide sequence selected from the group consisting of di-, tri- and tetra- microsatellite nucleotide repeat sequences to the DNA of the recombinant organism by a method such as microinjection, particle bombardment, liposome transfer, retroviral gene transfer. One representative technique for introducing the atypical interspersion pattern is disclosed by B. Lewin, GENES IV 699 et seq. (1990). Essentially, the technique involves injecting plasmids carrying the microsatellite repeat sequence into the germinal vesicle (nucleus) of the oocyte or pronucleus of a fertilized egg of the organism of interest. The egg is implanted into a pseudopregnant organism. After birth, the recipient organism is examined to see whether it has indeed gained the foreign DNA and, if so, whether it is expressed. If the microsatellite has been successfully inserted into the organism, it will be stably inherited by the progeny of that organism in a progeny-specific, individually invariant manner. The method could provide a useful tool for "branding" the recombinant population.

Other methods for introducing the atypical microsatellite sequence are disclosed in, for example, T. Ono et al., *A complete culture system for avian transgenesis, supporting quail embryos from the single-cell stage to hatching*, 161 Dev. Biol. 126–30 (Jan. 1994); P. Macri et al., *Transgenic animals as tools for investigating hepatocyte gene regulation and liver disease*, 11 Prog. Liver. Dis. 1–25 (1993); E. Behboodi et al., *Microinjection of bovine embryos with a foreign gene and its detection at the blastocyst stage*, 76 J. Dairy Sci. 3392 –9 (Nov. 1993); O. D. Wiestler et al., *Retrovirus-mediated oncogene transfer into neural transplants*, 2 Brain Pathol. 47–59 (Jan. 1992); J. Weis et al., *Integration site-dependent transgene expression used to mark subpopulations of cells in vivo: an example from the neuromuscular junction*, 2 Brain Pathol. 31–7 (Jan. 1992); R. B. Horsch, *Commercialization of genetically engineered crops*, 342 Philos. Trans. R. Soc. Lond. Biol. Sci. 287–91 (Nov. 29, 1993); A. Ritala et al., *Fertile transgenic barley to particle bombardment of immature embryos*, 24 Plant Mol. Biol. 317–25 (Jan. 1994); J. W. Gordon et al., *Transgenic animal methodologies and their applications*, 6 Hum. Cell 161–9 (Sept. 1993).

The present invention is further illustrated by the following non-limiting examples.

EXAMPLES

Example 1

DNA samples from various vertebrates (trout, frog, chicken, mouse, rat, cow, dog, African green monkey and human) were purchased from Oncor Incorporated, Gaithersburg, Maryland and Bios Corporation, New Haven, Connecticut. Mouse and dog DNA samples were prepared as previously described in B. Hershfield et al., Anim Genet 1993, 24, 293–295. A panel of DNA samples from unrelated humans and the DNA samples from different individual nonhuman primates (chimpanzee, orangutan, gorilla, rhesus macaque) were likewise purchased from Bios Corporation, New Haven, Connecticut.

PCR was carried out on 1 μg samples of each of the non-human DNA samples in a 100 μl reaction containing the primer 5'-GATCCACCAC CACCACCACC ACCAC-CACCA CCACCTAG-3' (SEQ. ID. NO. 1) at a concentration of 1.0 μM, 1X reaction buffer (which included 10 mM Tris-HCl (pH 8.3), 50 mM KCl, 1.5 mM $MgCl_2$, 0.01 weight/volume percent gelatin, 200 mM nucleotides, and 2.5 U Taq polymerase (from Perkin Elmer Cetus). A Techne PHC-2™ thermal cycler was programmed for 40 cycles of denaturation, annealing and extension. Each cycle included: (1) denaturation for one minute at 94° C., (2) annealing for one minute at 50° C., and (3) extension for one minute at 72° C., except that initial denaturation was for 2.5 minutes at 94° C. and the final extension was for 10 minutes at 72° C. Samples having a volume of 20 μl (⅕ the volume of the total reaction) were electrophoresed in 1.0 weight volume percent ("w/v%") agarose gels in 1X TBE (100 mM Tris (hydroxymethyl)aminomethane (also known as "Tris buffer"), 90 mM boric acid, 1 mM ethylenediaminetetraacetic acid (pH 8.4)). The gels were stained with ethidium bromide and the DNA visualized by illumination with short-wave UV.

Sample 1 of FIG. 1 corresponds to a reference marker which provides reference points to facilitate determination of the size of the interspersion patterns of the $(CAC)_n$ repeat in the vertebrate samples illustrated in Samples 3 through 10. Sample 1 is a 100 bp ladder marker (1 μg total) whose three most intense bands were (as shown in FIG. 1) of 600 bp, 1500 bp, and 2072 bp (uncut vector). Samples 2 through 9 corresponded to the following vertebrate species:

2 ... Rainbow trout (*Salmo gairdneri*)
3 ... Frog (*Xenopus*)
4 ... Chicken (*Gallus gallus*)
5 ... Rat (*Rattus*)
6 ... Cow (*Bos taurus*)
7 ... Dog (*Canis familiaris*)
8 ... African green monkey (*Cercopithecus aethiops*)
9 ... Mouse (*mus musculus*)

The results of the electrophoretic analysis are summarized by Table 1 below and illustrated by FIG. 1, a photograph of the results of the $(CAC)_n$ amplification and electrophoretic analysis performed on DNA from individuals of several non-human vertebrate species.

TABLE I

| Sample | Species | Product Sizes (in kb) |
|---|---|---|
| 2 | Trout | 2.5, 1.5 |
| 3 | Frog | 2.4, 2.2, 1.3, 1.1 |
| 4 | Chicken | 3.2, 2.0, 1.5 |
| 5 | Rat | 3.0, 2.3, 1.9[a], 1.7, 1.6, 1.4, 1.2[a], 1.1, 1.0 |
| 6 | Cow | 2.2 |
| 7 | Dog | 2.2, 2.0, 1.9, 1.6, 1.3, 1.1 |
| 8 | African green monkey | 2.7[a], 2.4, 1.7, 1.3 |
| 9 | Mouse[b] | 2.5, 2.3, 2.1, 1.9, 1.7, 1.6, 1.4, 1.0 |

[a]Cryptic allele of slightly larger size (ca. 50 bp) also noted.
[b]Mouse results not illustrated in FIG. 1.

As shown by FIG. 1 and Table 1, PCR amplification was conducted on DNA from representative fish, amphibians, birds, and mammals (including rodents, ruminants, carnivores, and primates). In trout and frogs, only weak amplification was noted. In the other species, the average number of bands noted was between 3 and 6 (although cows had only one band and the rodents exhibited eight bands). The bands ranged in size from 3.2 kb (chicken) to 1.0 kb (rat). The bands were markedly discrete and scorable, with clear differences between the species evident by visual inspection. The relative intensities of the PCR products were greatest in mammals, indicating that the relative amount of amplification was greatest in the mammalian species.

Example 2

To test the reproducibility and variability of the patterns among individuals of a single species, PCR amplification was performed on DNA samples from 20 unrelated humans (10 Caucasian, 3 Negro, 7 Oriental) and from non-human primates. The preparation of the DNA samples, PCR amplification methodology, and electrophoretic analysis was conducted as described in Example 1, above.

Figure 2:
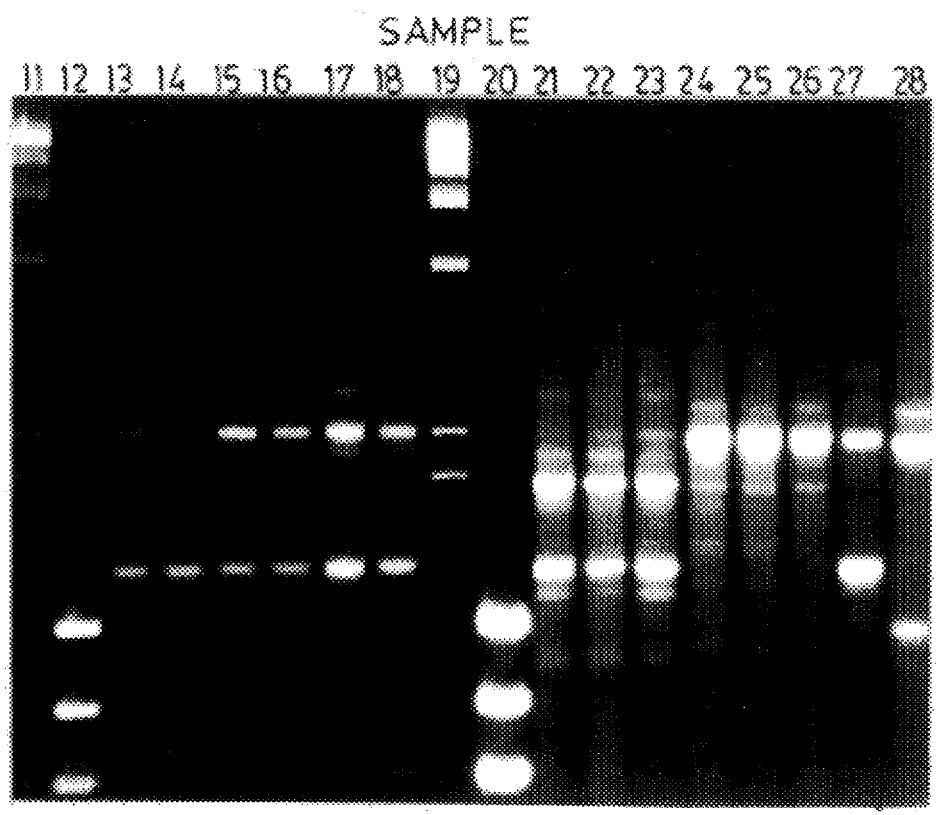
FIG. 2 is a photograph of the results of the $(CAC)_n$ amplification and electrophoretic analysis performed on DNA taken from several unrelated human individuals and individuals from other non-human primate species.

Samples 11 and 12 of FIG. 2 correspond to reference markers used as reference points to facilitate determination of the size of the interspersion patterns of the $(CAC)_n$ repeat in the vertebrate samples illustrated in Samples 11 through 28. Samples 11 and 19 correspond to λ/HindIII marker (available from GIBCO/BRL), and exhibited bands (as shown in FIG. 2) of 23.6, 9.6, 6.6, 4.3, 2.3, and 2.0 kb. Samples 12 and 20 correspond to ΦX174/HaeIII marker (available from GIBCO/BRL) and exhibited amplification bands (as shown in FIG. 2) of 1353, 1078 and 872 bp. Samples 13 through 18 and 21 through 28 correspond to the PCR amplification product of the following primate samples:

```
13 ... Caucasian #1
14 ... Caucasian #2
15 ... Negro #1
16 ... Negro #2
17 ... Oriental #1
18 ... Oriental #2
21 ... Chimpanzee #1
22 ... Chimpanzee #2
23 ... Chimpanzee #3
24 ... Orangutan #1
25 ... Orangutan #2
26 ... Orangutan #3
27 ... Gorilla (Gorilla gorilla)
28 ... Rhesus macaque (Macaca mulatta).
```

The results of the electrophoretic analysis are summarized in Table II below and illustrated by FIG. 2, a photograph of the results of the $(CAC)_n$ amplification and electrophoretic analysis of DNA taken from several unrelated human individuals and individuals from other non-human primate species.

TABLE II

| Sample | Species | Product Sizes (in kb) |
|--------|---------|-----------------------|
| 13–18  | Human   | 2.5, 2.2, 2.1, 1.6 |
| 21–23  | Chimpanzee | 2.5, 2.2, 2.1, 2.0, 1.6, 1.5, 1.2 |
| 24–26  | Orangutan | 2.5, 2.2, 2.0, 1.7*, 1.5 |
| 27     | Gorilla | 2.2, 1.5 |
| 28     | Rhesus macaque | 2.4, 2.2, 1.3 |

*Cryptic allele of slightly larger size (ca. 50 bp) also noted.

As illustrated by FIG. 2, highly similar interspersion patterns were found for each tested individual within a species. For example, Samples 13–18 each contained four bands of about 2.8 kb, 2.5 kb, 2.3 kb and 1.6 kb, respectively. On the other hand, as clearly illustrated by FIG. 2 and Table II above, the interspersion pattern between different primate species was very different.

FIG. 2 illustrates the consistency of the interspersion patterns from six representative unrelated human samples (two from each tested racial backgrounds). Amplification patterns that were highly similar for different individuals within a species and markedly different between species were also noted for orangutans and chimpanzees and gorillas. We have performed similar tests on 10 dogs from 7 breeds and in this species also have seen highly similar amplification patterns between different individuals (results not shown).

The amplification products noted in the samples discussed above are due to true binding between the primer and homologous sequences in the genomes of the tested species. Consequently, the present method differs in many significant ways from arbitrarily primed PCR (hereafter "AP-PCR", described in, for example, Welsh, J., and McClelland, M., *Nucl Acids Res* 1990, 18, 7213–7218), randomly amplified polymorphic DNA (hereafter "RAPD", described in, for example, Williams, J. G. K., Kubelik, A. R., Livak, K. J., Rafalski, J. A., and Tingey, S. V., *Nucl. Acids Res.* 1990, 18, 6531–6535), and DNA amplification fingerprinting (hereafter "DAF", described in, for example, Caetano-Anolles, G., Bassam, B. J., and Gresshoff, P. M., *Biotechnology* 1991, 9, 553–557).

Initially, in the known processes for analyzing DNA, there is marked variability in amplification patterns between individuals of the same species (e.g., DAF) and between strains of the same species (e.g., AP-PCR). In the present method, the only differences noted are between species. Second, the previous methods produce complex patterns that are difficult to interpret, whereas the patterns of the present method are simple and easy to interpret. Lastly, the other methods all rely upon relaxing the PCR conditions by conducting the initial rounds of primer annealing at reduced temperatures (as low as 30° C.), in the presence of high concentrations of $MgCl_2$, and/or very high ratios (in excess of 100,000:1) of primer to DNA template. In the known processes, the PCR conditions have been relaxed to encourage nonhomologous binding between primer and template. However, it has been shown that the application of relaxed PCR conditions can result in serious artifactual variation of results due to inconsistencies in primer-to-template ratios, differences in annealing temperatures, and minute variations in magnesium concentration (see, e,g., Ellsworth, D. L., Rittenhouse, K. D., and Honeycutt, R. L., 14 *BioTechniques* 214–217 (1993)).

It is believed that because the present method is based on true homology of primer and template, standard PCR annealing conditions, standard primer-to-template ratios, and lower concentrations of magnesium can be advantageously used. Accordingly, it is clear that PCR amplification of DNA can be a useful diagnostic test for identifying which species contributed to a biological sample. In all of the tested vertebrates (except fish), a confined number of distinct bands was noted and the number of bands was not directly related to the complexity of the organism's genome. Consequently, the method of the present invention will be useful relative to a broad range of different species.

In addition, the band pattern is not indicative of the genetic heterogeneity of the species. In other words, as evidenced by the inbred mouse strain having as complex a pattern as any other species, increased inbreeding does not reduce the number of reproducible bands. Furthermore, the band pattern, although highly similar between individuals of the same species, could appear markedly different even between such closely related species as chimpanzee and man.

Lastly, the PCR-based technique described in Examples 1 and 2 necessitates having only small amounts of DNA, allowing for definitive species identification to be advantageously made from concomitantly small tissue samples.

Example 3

To test the ability to identify and distinguish contributors to a mixed DNA sample, PCR amplification was performed on mixtures of human and dog DNA and mixtures of human and chimpanzee DNA. The preparation of the DNA samples, PCR amplification methodology, and electrophoretic analysis was conducted as described in Example 1, above. Sample 29 corresponds to µHind/III marker (available from GIBCO/BRL) and exhibited bands (as shown in FIG. 4) of 23.6, 9.6, 6.6, 4.3, 2.3, and 2.0 kb. Sample 30 corresponds to a 100 bp ladder marker and its three most intense bands were of 600, 1500 and 2072 bp (uncut vector). The DNA contained in each Sample is shown by Table III below. The results of the electrophoretic analysis are illustrated by FIG. 3, a photograph of the results of the $(CAC)_n$, amplification and electrophoretic analysis performed on DNA mixtures containing DNA from human and non-human species to identify the individual contributors to the DNA mixture.

TABLE III

| Sample | Species |
|---|---|
| 29 | MARKER |
| 30 | MARKER |
| 31 | Individual Human |
| 32 | Individual Chimpanzee |
| 33 | Human/Chimpanzee Mix |
| 34 | Human/Dog Mix |

Figure 3:
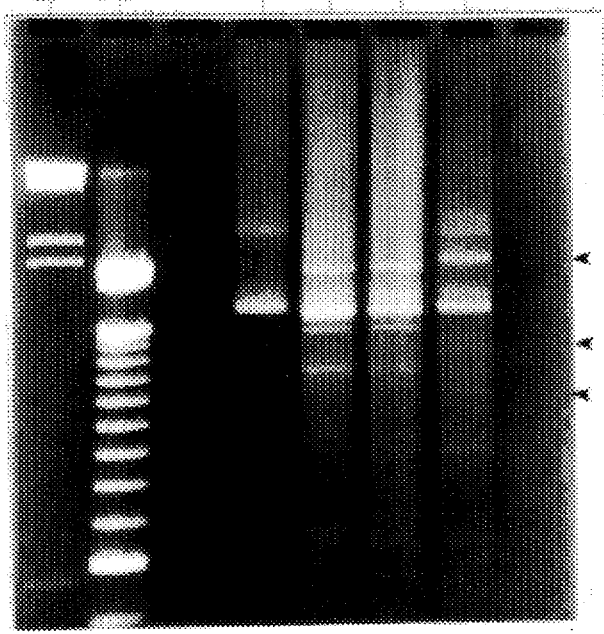
FIG. 3 is a photograph of the results of the $(CAC)_n$ amplification and electrophoretic analysis performed on DNA mixtures containing DNA from both human and non-human species to identify the individual contributors to the DNA mixture.
Figure 4:
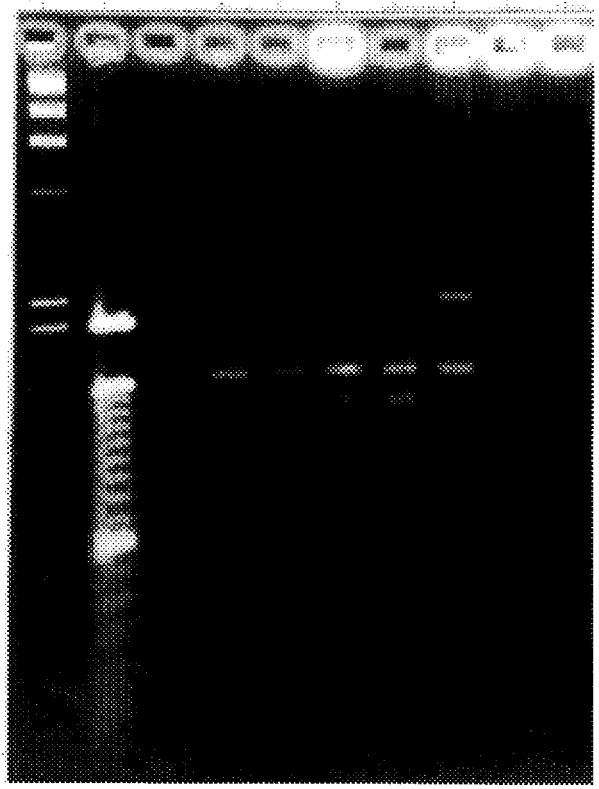
FIG. 4 is a photograph of the results of the $(CAC)_n$ amplification and electrophoretic analysis performed on DNA from unrelated humans under varying $Mg^{+2}$ and pH conditions.

As shown by FIG. 3, chimpanzee and human amplification profiles are similar except the chimpanzee pattern contains an extra band at 2.0 kb, denser (i.e., more intense) bands at 1.5 kb and 1.2 kb (which are minor components of the human amplification profile), and a lighter band at 2.2 kb. Thus, in a mixture of human and chimpanzee DNA, chimpanzee DNA should be distinguishable by the presence of a 2.0 kb bands in the amplification product and human DNA should be distinguishable by an increase in the intensity of the 2.2 kb band. Referring to FIG. 3, however, reveals that the amplification profile for the human/chimpanzee mix (Sample 33) is indistinguishable from the chimpanzee control amplification profile (Sample 32). Thus, in the case of species differing by the presence or absence of a single band and/or amplification intensity differences, the species missing the additional band should not be ruled out. Accordingly, in such a case the present process would serve as an initial screening tool. Further differentiation of the the sample (i.e., to distinguish human and chimpanzee DNA) can be accomplished through additional tests (e.g., analysis for human blood groups).

Dog and human DNA amplification patterns are very different and each species contributes unique bands to the amplification pattern, as shown by FIG. 1, Sample 9 (dog DNA) and FIG. 3, Sample 31. Reference to FIG. 3, Sample 34, the amplification product of a human/dog DNA mixture, indicates that both dog and human DNA are both present in that sample. The arrows on FIG. 3 indicate the prominent dog-specific bands that can be used to identify dog DNA's presence in the mixture of Sample 34. The presence of the 2.5, 2.2, and 2.1 kb bands (and absence of the 1.5 kb and 1.2 kb bands) confirms the presence of human DNA and eliminates the possibility of the presence of chimpanzee DNA in the DNA mixture of Sample 34. Accordingly, as illustrated by Example 3, the methods of the present invention can be advantageously used to distinguish the DNA of different animal species contributing to a sample of DNA

Example 4

To test the effect of variable magnesium ion concentrations on the method of the present invention, PCR amplification was performed on DNA samples from 7 unrelated humans under varying PH and magnesium conditions. The preparation of the DNA samples, PCR amplification methodology, and electrophoretic analysis was conducted as described in Example 1, above. Sample 35 corresponds to µ/HindIII marker (available from GIBCO/BRL) and exhibited bands (as shown in FIG. 4) of 23.6, 9.6, 6.6, 4.3, 2.3, and 2.0 kb. Sample 36 corresponds to a 100 bp ladder marker and its three most intense bands were of 600, 1500 and 2072 bp (uncut vector). The details of each amplification are shown by Table IV below, where the magnesium chloride concentration (expressed as millimolarity "mM") in the reaction is represented as [$MgCl_2$]. The results of the example are illustrated by FIG. 4, which is a photograph of the results of the $(CAC)_n$ amplification and electrophoretic analysis performed on DNA from unrelated humans under varying $Mg^{+2}$ and pH conditions.

TABLE IV

| Sample | Species | [$MgCl_2$] | pH |
|---|---|---|---|
| 35 | MARKER | — | — |
| 36 | MARKER | — | — |
| 37 | Human | 1.5 | 8.5 |
| 38 | Human | 2.0 | 8.5 |
| 39 | Human | 2.5 | 8.5 |
| 40 | Human | 3.5 | 8.5 |
| 41 | Human | 2.0 | 9.0 |
| 42 | Human | 2.0 | 9.5 |
| 43 | Human | 2.0 | 10.0 |

As illustrated by FIG. 4, low magnesium concentrations and at relatively lower pHs in the PCR methods of the present invention encourage homologous binding and provide the species specific-individually invariant amplification patterns that allow species differentiation in a DNA-containing biological sample. At higher magnesium concentrations (e.g., Sample 40, having a [$MgCl_2$] of 3.5 mM and pH 8.5), artifactual bands occurred which decrease the clarity and reliability of the results. At a constant magnesium concentration of 2.0 mM and increasingly basic pH (Samples 38, 41–43) amplification in the pH 9.0 buffer (Sample 41) was similar to that seen in the pH 8.5 buffer (Sample 38). However, no significant amplification was seen in the pH 9.5 or pH 10.0 buffers (Samples 42 and 43), suggesting that the present process is preferably carried out at pHs less than about 9.5.

Although the present invention has been described in detail for the purposes of illustration, it is understood that such detail is solely for that purpose, and variations can be made therein by those skilled in the art without departing from the spirit and scope of the invention which is described by the following claims.

What is claimed is:

1. A method of identifying the species origin of a DNA sample from a DNA-containing organism comprising the steps of:
    providing a sample of DNA from a DNA-containing organism, said DNA having a nucleotide sequence that comprises microsatellite repeat sequences separated by intervening non-repeating nucleotides, wherein said DNA-containing organism is a species selected from the group consisting of *Salmo gairdneri, Gallus gallus, Bos taurus, Canis familiaris, Cercopithecus aethiops, Mus musculus, Gorilla gorilla, Macaca mulatta* and *Homo sapiens;*
    determining an interspersion pattern for said DNA sample, said interspersion pattern representing a pattern of said intervening non-repeating nucleotides in said DNA sample, wherein said interspersion pattern is characteristic of the species of origin of said DNA sample, wherein said species of origin is selected from the group consisting of trout, chicken, rat, cow, dog, african green monkey, mouse, human, chimpanzee, orangutan, gorilla, and Rhesus macaque; and
    comparing said determined interspersion pattern with known interspersion patterns of said selected species, wherein identification of a known interspersion pattern of one of said selected species as identical to said determined interspersion pattern identifies the species origin of said DNA from said sample as the species of the one of said selected species.

2. A method according to claim 1, wherein said microsatellite repeat sequences are selected from the group consisting of $(CA)_n$, $(CAC)_n$, $(GATA)_n$, $(GT)_n$, $(TCC)_n$, $(AGG)_n$, $(GTG)_n$, and $(CTAT)_n$, and wherein n is greater than or equal to 2.

3. A method according to claim 2, wherein said microsatellite repeat sequences are $(CAC)_n$ or $(GTG)_n$, and wherein n is greater than or equal to 2.

4. A method according to claim 3, wherein said oligonucleotide primer has the sequence according to SEQ. ID. NO. 1.

5. A method according to claim 1, wherein said microsatellite repeat sequences are selected from the group consisting of di-, tri- and tetra-microsatellite repeat sequences.

6. A method according to claim 1, wherein said species of origin is human.

7. The method of claim 1 wherein determining an interspersion pattern comprises using an oligonucleotide primer having a DNA sequence consisting of said microsatellite repeat sequence to amplify said intervening non-repeating nucleotides separating said microsatellite repeat sequences, and determining the interspersion pattern based on said amplified intervening non-repeating nucleotides.

8. The method of claim 7 wherein using an oligonucleotide primer comprises using said oligonucleotide primer in a polymerase chain reaction to amplify said intervening non-repeating nucleotides.

9. The method of claim 8, wherein said polymerase chain reaction comprises the steps of:
    denaturing said DNA sample for a time and temperature effective to cleave complementary strands of said DNA sample and form separated strands of said DNA sample;
    annealing said separated strands with said oligonucleotide primer to anneal said oligonucleotide primer to complementary base pairs on said strand of said DNA sample and produce a complementary strand of said DNA sample;
    extending said complementary strand of said DNA sample; and
    repeating said denaturing, said annealing and said extending steps a sufficient number of cycles to produce an amplification product capable of being analyzed to determine an interspersion pattern for said DNA sample, said amplification product consisting of amplified intervening non-repeating nucleotides.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GATCCACCAC CACCACCACC ACCACCACCA CCACCTAG        3 8